United States Patent
Reutter et al.

(12)

(10) Patent No.: US 6,692,931 B1
(45) Date of Patent: Feb. 17, 2004

(54) RECOMBINANT GLYCOPROTEINS, METHOD FOR THE PRODUCTION THEREOF, MEDICAMENTS CONTAINING SAID GLYCOPROTEINS AND USE THEREOF

(75) Inventors: Werner Reutter, Thielallee 66, D-14195 Berlin (DE); Rudolf Tauber, Berlin (DE); Rüdiger Horstkorte, Berlin (DE); Sabine Nöhring, Seeburg (DE); Martin Gohlke, Berlin (DE); Rolf Nuck, Berlin (DE); Richard R. Schmidt, Constance (DE); Charlotte Hauser, München (DE)

(73) Assignee: Werner Reutter, Berlin (DE)

( * ) Notice: Subject to any disclaimer, the term of this patent is extended or adjusted under 35 U.S.C. 154(b) by 0 days.

(21) Appl. No.: 09/831,868

(22) PCT Filed: Nov. 16, 1999

(86) PCT No.: PCT/EP99/08787

§ 371 (c)(1),
(2), (4) Date: Dec. 13, 2001

(87) PCT Pub. No.: WO00/29567

PCT Pub. Date: May 25, 2000

(30) Foreign Application Priority Data

Nov. 16, 1998 (DE) .......................................... 198 52 729

(51) Int. Cl.$^7$ ........................... C12Q 1/56; A61K 38/16
(52) U.S. Cl. ............................................. 435/13; 514/8
(58) Field of Search ................................ 514/8; 435/13

(56) References Cited

FOREIGN PATENT DOCUMENTS

WO  94/24167  10/1994

OTHER PUBLICATIONS

M. Gohlke et al., Chemical Abstracts, vol. 126, No. 19, pp. 67–77, Abstract No. 246554 (1997).

*Primary Examiner*—Hankyel T. Park
(74) *Attorney, Agent, or Firm*—Wenderoth, Lind & Ponack, L.L.P.

(57) ABSTRACT

The invention relates to novel recombinant glycoproteins that act as messenger substances, signaling substances, promoters, stimulators and initiators in a multitude of ways in the animal, especially human, circulation system. The invention also relates to a method for the production thereof, pharmaceutical agents containing said glycoproteins and the use thereof The invention more particularly relates to novel recombinant human glycoproteins (rh glycoproteins), preferably novel rh differentiation factors, especially rh erythropoietin; novel rh growth factors, especially rh CSF (colony stimulating factor), rh GMCSF (granulocytes monocytes stimulation factor); novel rh thrombolytic agents, especially rh tPA (tissue plasminogen activator) and rh urokinase; novel rh thromboprophylactic agents, especially rh antithrombin III; novel rh coagulation factors, especially rh factor VIII and rh factor IX; novel rh interferons, especially rh α, β and γ interferons; and novel rh interleukins, especially rh IL-2, IL-15, IL-16 and IL-17. The invention further relates to a method for the production of said substances, pharmaceutical agents containing them and to the use thereof.

43 Claims, No Drawings

RECOMBINANT GLYCOPROTEINS, METHOD FOR THE PRODUCTION THEREOF, MEDICAMENTS CONTAINING SAID GLYCOPROTEINS AND USE THEREOF

The invention relates to novel recombinant glycoproteins that act as messenger substances, signaling substances, promoters, stimulators and initiators in a multitude of ways in th animal, especially human, circulation system; to processes for their preparation, to pharmaceutical compositions containing them and to their uses. The invention in particular relates to new recombinant human glycoproteins (rh glycoproteins), preferably novel rh differentiation factors, especially rh erythropoietin; to novel rh growth factors, especially rh CSF (colony-stimulating-factor), rh GMCSF (granulocytes-monocytes-stimulating factor); to novel rh thrombolytic agents, especially rh tPA (tissue-plasminogen-activator) and rh urokinase; to novel rh thromboprophylactic agents, especially rh antithrombin III; to novel rh coagulation factors, especially rh factor VIII and rh factor IX; to novel rh interferons, especially rh $\alpha$-, $\beta$- and $\gamma$-interferons; and to novel rh interleukins, especially rh IL-2, IL-15, IL-16 and IL-17; to processes for their preparation; to novel pharmaceutical compositions containing them and to the uses thereof.

Glycoproteins are proteins containing covalently-bound carbohydrates (sugars). Glycoproteins, especially human glycoproteins, act as messenger substances, signaling substances, promoters, stimulators and initiators in metabolic processes of animals and human beings, which directly or indirectly influence these metabolic processes. Usually they are formed in vivo in the body or biosynthetically and, after having fulfilled their specific function, they are again excreted thereof or broken down therein. The glycoproteins having been formed in a natural way within the body (so called "native glycoproteins") are characterized in that they are substituted at the amine group of the aminoglycan radical by an acetyl group. These native glycoproteins formed in a natural manner in vivo or by biosynthesis (see German patent 4 311 580) in human and animal are effective means for stimulating the growth and the differenciation of human and animal cells of the immune system and for inhibiting the adhesion of leucocytes, thrombocytes and tumor cells at the endothelial cells of blood vessels; for stimulating the immune system, especially the T-lymphocytes, for defense against infection, for treating immune deficiencies, tumor diseases including metastasing processes, infectious diseases and circulatory collapse, especially occlusions of vessels and septicemia; for inhibiting the bonding of a ligand at its sialylated cell surface receptor to a host cell; for inhibiting the bonding of a microphage or a toxin to the host cell via a sialylated receptor by an in vivo-modulation of neuraminic acids; for the biosynthetic preparation of ligands or receptors having a modified neuraminic acid radical and for the use thereof for the competition of physiological or pathological ligand-receptor-interactios; for influencing in vitro the course of infection by human immunodeficiency viruses as well as the in vivo-prevention of an infection by human immunodeficiency viruses; and for the treatment of parasitic diseases.

The glycoproteins occuring in animal organisms are important components of cell membranes as well as soluble components of body fluids and of the extracellular matrix. The carbohydrates are linked to form chains (oligosaccharides) and they can be linked to the protein backbone in different ways. As important components of the cell membrane they contain sialic acid (derivatives of 2-keto-3-deoxy-D-glycero-D-galacto-nonulopyranosidonic acid (KDN)), which plays an important role in biological processes.

The oligosaccharides of glycoproteins are classified according to their mode of linkage to the protein. The oligosaccharide of thioacidglycoproteins are mostly bound N-glycosidically to an asparagine radical of the polypeptide chain (N-glycans). This group comprises dissected glycoproteins having different functions, e.g. soluble enzymes, immunoglobulins and hormones on the one hand, and membrane glycoproteins, e.g. membrane enzymes, transport proteins as well as receptor proteins on the other hand. A further group are the oligosaccharides which are bound O-glycosidically via a galatose, N-acetyl-galactosamine or xylose radical to a serine- or threonine radical of the polypeptide chain (O-glycans). They occur together with N-glycans also in immunoglobulins and other glycoproteins. The O-glycans also comprise the oligosaccharides of proteoglycans which are characterized by a particularly high proportion of carbohydrates. In these glycoconjugates occuring in the extracellular matrix the oligosaccharides can be bound via a galactose, N-acetylgalactosamine or xylose radical to a polypeptide backbone.

The glycoproteins consisting of monosaccharides and protein often are summarized with the glycolipids as glycoconjugates. The sugar component of the glycoproteins comprising, with a few exceptions, less than 50% of the total glycoproteins are linked via splittable O- or N-glycosidic bonds to the peptide part. As carbohydrates in the glycoproteins hexoses (galactose, mannose, more seldom glucose), N-acetylhexosamines, N-acetylneuraminic acid, fucose and others can be found. For identification and determination of the glycoproteins mainly affinity chromatography using plant lectins as ligands (e.g. concanavalin A, wheat germ agglutinins and others) is suited.

Almost all membrane glycoproteins, serum proteins, plasma proteins, and blood group substances are glycoproteins as are many enzymes and proteohormones, all antibodies, the chalones, mucins, lectins, bindins, fibronectins, the intrinsic factor and similar proteins. As membrane or cell surface proteins some glycoproteins play an important role in the pathogenicity of viruses. In this case, as in other receptor-specific cellular interactions, the carbohydrate components are responsible for the recognition process at the molecular level. Some bacteria and viruses adhere to their target cells via specific sugar structures on receptors.

Oligosaccharide structures are particularly important also in view of cell-cell and cell-matrix interactions. Thus, the oligosaccharides of glycoproteins mediate the adhesion of neuronal cells and the bonding of lymphocytes to specific endothelial cells. Furthermore, oligosaccharides can serve as the antigenic determinants of glycoproteins. Also during embryogenesis and organogenesis, carbohydrate-carbohydrate interactions are essential to specific cell recognition. The malignant transformation of cells is accompanied by characteristic changes in the oligosaccharide structures of glycoproteins. The extent to which altered oligosaccharide structures of membrane and intercellular glycoproteins of tumor cells are the cause or result of tumorigenesis and metastasis is not known until yet.

For the treatment of diseases related to the immune system, substances have to be administered that reinforce the immune response by stimulating the cells of the immune system. The search for active substances that stimulate the immune system is therefore a preferred goal of pharmacological research. Active immunstimulants having minimal side effects, however, are not known until yet.

Therefore, the object of the invention was to find new substances by means of which it is possible to influence the metabolic processes controlled by glycoproteins as messenger substances, signaling substances, promoters, stimulators and initiators, more effectively, more specifically and more selectively than until today. It was in particular the object of the invention to find such novel glycoproteins acting as messenger substances, signaling substances, promoters, stimulators and initiators in human and animal metabolism and which can be administered in lower doses and therefore have lower side effects than the corresponding native substances.

Now it has been found that this object can be achieved according to the present invention by novel glycoproteins which are different from the abovementioned native glycoproteins in that the naturally occurring acetyl substitution in the aminoglycan radical ist repaced by other acyl groups, in particular by a ($C_3$–$C_7$)-acyl group or a hydrocarbyl group, especially a ($C_3$–$C_7$)-alkyl, -alkenyl or -alkinyl group. In fact, it has been shown that the thus obtained novel compounds exhibit an altered, in particular a longer, pharmacokinetics, compared with the biological half-life time of the corresponding, already known and commercially available native glycoproteins having an N-acetyl group in their aminoglycan radical. These novel glycoproteins can be prepared in a manner as described below, in particular by genetic engineering where recombinant glycoproteins, especially recombinant human glycoproteins (rh glycoproteins) are obtained.

Due to their altered, especially longer, pharmacokinetics these substances can be used in substantially lower doses which result in substantially reduced undesired side effects compared with those found by using the corresponding native substances. This applies in particular when the novel glycoproteins are used in a form which is mono- or poly-acylated, preferably -acetylated, at the OH groups of the monosaccharide part.

Subject-matter of the present invention are according to a first aspect novel recombinante glycoproteins, especially rekombinant human glycoproteins (rh slycoproteins) having the general formula (I)

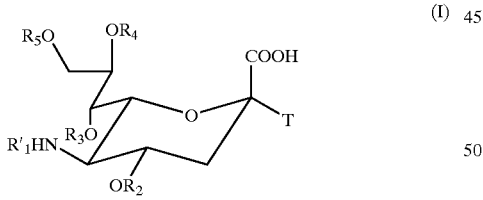

(I)

wherein:

$R'_1$ is a linear or cyclic, unbranched or branched, optionally mono- or poly-hydroxylated and/or -ketylated ($C_3$–$C_7$)-acyl radical, in particular ($C_3$–$C_7$)-alkanoyl radical, or a linear or cyclic, unbranched or branched, optionally mono- or polyhydroxylated and/or -ketylated ($C_3$–$C_7$)-hydrocarbyl radical, in particular ($C_3$–$C_7$)-alkyl, -alkenyl or -alkinyl radical;

$R_2$, $R_3$, $R_4$ and $R_5$, which can be the same or different, each are hydrogen, a linear or branched alkyl radical having 1 to 20 carbon atoms ($C_nH_{2n+2}$; n=1 to 20); a linear or branched alkenyl radical having 3 to 20 carbon atoms ($C_nH_{2n}$; n=3 to 20, the position of the double bond at $C_n$ is at n=2 to 19); a linear or branched alkinyl radical having 3 to 20 carbon atoms $C_nH_{2n-2}$, n=3 to 20, the position of the triple bond at $C_n$ is at n=2 to 19); an alkenyl or alkinyl radical having 2 or more double bonds and triple bonds, respectively, and having 4 to 20 carbon atoms; an aryl radical having 6 to 20 carbon atoms; a linear or branched, saturated or mono- or poly-unsaturated acyl radical (—CO—$R_1$) having in total 1 to 20 carbon atoms, including the mono- or poly-hydroxylated analogues thereof; an aroyl radical having 6 to 20 carbon atoms; a carbonylamide radical of formula —$CONH_2$ or —$CONHR_1$; a linear or branched, saturated or mono- or poly-unsaturated thioacyl radical (—CS—$R_1$) having in total 1 to 20 carbon atoms; or a thiocarbamide radical of formula —CS—$NH_2$ or —CS—$NHR_1$;

where $R_1$ each represents hydrogen, a linear or branched, saturated or mono- or poly-unsaturated alkyl radical having 1 to 20 carbon atoms and where each of the above-mentioned radicals with the exception of H optionally can be mono- or poly-substituted by halogen, hydroxy, epoxy, amine, mercaptan, phenyl, phenol or benzyl groups and T is a mono- or di- or oligo-saccharide radical having up to 40 glycosidically linked, optionally branched sugar radicals, the saccharide radical containing furanose and/or pyranose rings and containing 5 to 230 carbon atoms and being N- or O-glycosidically bound to polypeptides.

The preferred meanings in the above general formula (I) are as follows:

$R_2$, $R_3$, $R_4$ and $R_5$, which can be the same or different, each represent hydrogen, a linear or branched alkyl radical having 1 to 7 carbon atoms; a linear or branched alkenyl radical having 3 to 10 carbon atoms; a linear or branched alkinyl radical having 3 to 10 carbon atoms; an alkenyl or alkinyl radical having 2 or more double bonds and triple bonds, respectively, and having 7 to 12 carbon atoms; a phenyl radical; a linear or branched, saturated or mono- or polyunsaturated acyl radical (—CO—$R_1$) having in total 1 to 7 carbon atoms, in particular an acetyl radical, including mono- or poly-hydroxylated analogues thereof; an aroyl radical having 6 to 10 carbon atoms; a carbonylamide radical of formula —$CONH_2$ or —$CONHR_1$; a linear or branched, saturated or mono- or poly-unsaturated thioacyl radical (—CS—$R_1$) having in total 1 to 7 carbon atoms; or a thiocarbamide radical of formula —CS—$NH_2$ or —CS—$NHR_1$;

where $R_1$ each represents hydrogen or a linear or branched, saturated or mono- or poly-unsaturated alkyl radical having 1 to 20 carbon atoms and where each of the above-mentioned radicals with the exception of H optionally can be mono- or poly-substituted by fluorine, chlorine, bromine or iodine, hydroxy, epoxy, amine, mercaptan, phenyl, phenol or benzyl groups.

According to a further preferred embodiment of the invention in general formula (I)

T represents a saccharide radical having an N-glycan structure of formula (Ia)

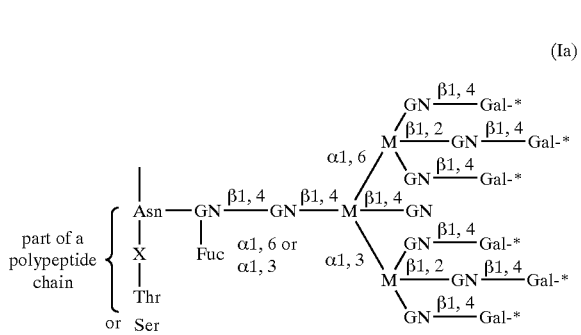

(Ia)

where:
Gal = galactose,
GN = N-acetyl-D-glucosamine,
M = D-mannose,
Fuc = fucose,
Asn = asparagine,
X = any amino acid with the exception of proline,
Thr = threonine,
Ser = serine,
* = attachment site of T (1 to 6 molecule radicals), in which both peripheral radicals M can be substituted by 1 to 3 trisaccharides;
or T represents a saccharide radical having an O-glycan structure of formula (Ib):

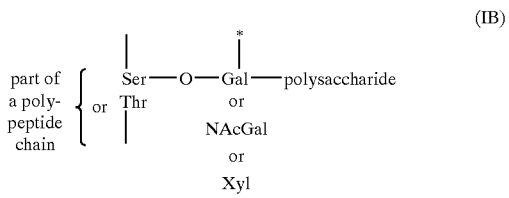

(IB)

where:
Gal = galactose
Thr = threonine
Ser = serine
Xyl = xylose
NAcGal = N-acetyl-galactosamine
* = attachment site of T, where in the above formulae (Ia) and (Ib) galactose (Gal) can be replaced by 2-deoxy-galactose or 2-deoxy-2-halide (F, Cl, Br, I)-galactose.

In particular, when T represents a saccharide radical having an N-glycan structure or represents a saccharide radical having an O-glycan structure, then GN preferably represents a radical of general formula (II):

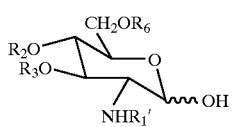

(II)

wherein $R'_1$, $R_2$ and $R_3$ have the meanings given above, $R_6$ has the same meanings as $R_2$ and $R_3$ and $-NHR_1$ besides the equatorial position can also occupy an axial position and wherein furthermore $-OR_2$ can occupy the axial position if $-NHR'_1$ takes an equatorial position, and wherein one or more or all of the groups $-OR_2$, $-OR_3$, $-OR_6$ and/or the free OH group can be acylated by a linear or branched, saturated or mono- or poly-unsaturated acyl radical ($-CO-R_1$) having in total 1 to 20, especially 1 to 7 carbon atoms, and preferably can be acylated by the acetyl radical ($-CO-CH_3$); including all mono- or polyhydroxylated analogues thereof.

The above mentioned radicals $R_1$ to $R_6$ preferably represent H or $CH_3$ or ($C_1-C_7$)-acyl, especially acetyl.

In the $NHR'_1$-group $R'_1$ preferably represents a ($C_3-C_7$)-acyl radical selected from the group consisting of propanoyl, isopropanoyl, pivaloyl and pivanoyl (tert-butyl-carbonyl), respectively, cyclopropanoyl, butanoyl, pentanoyl, hexanoyl, heptanoyl, crotonoyl and laevulinoyl, and/or a ($C_3-C_7$)-hydrocarbyl radical selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof.

The above-mentioned novel compounds of the invention exhibit an altered, especially longer, pharmacokinetics, compared with the biological half-life time of the corresponding, already known and commercially available natural (native) glycoproteins having $R'_1$=acetyl.

The novel compounds of the invention preferably are
recombinant glycoprotein, especially a recombinant human glycoprotein (rh glycoprotein), preferably rh differentiation factors, in particular rh erythropoietin;
rh growth factors, in particular rh CSF (colony-stimulating-factor), rh GMCSF (granulocytes-monocytes-stimulating-factor);
rh thrombolytic agents, in particular rh tissue-plasminogen-activator (tPA) and rh urokinase;
rh thromboprophylactic agents, in particular rh antithrombin III;
rh coagulation factors, in particular rh factor VIII and rh factor IX;
rh interferons, in particular rh α-, β- and γ-interferons; and
rh interleukins, in particular rh IL-2, IL-15, IL-16 and IL-17.

The aboved-defined novel recombinant glycoproteins, especially rh glycoproteins, of the invention are novel classes of substances which can be used as potent active ingredients for the treatment of diseases where cells of the specific and unspecific immune defense, tumor cells, leucocytes, thrombocytes and endothelial cells of blood vessels are involved. The novel compounds of the invention can specifically act via a modulation of the receptors on membranes which are involved in the regulation of the growth and the differentiation as well as the adhesion of cells of the immune system, of tumors and blood vessels. An immunostimulation is necessary in therapeutic processes for infectious and tumor-related diseases. Furthermore, the novel compounds of the invention inhibit the adhesion of leucocytes or tumor cells at the andothelial cells of blood vessels in the case of a septic shock or metastatis. The administration application of these substances can be made in a clearly lower dose due to their longer biological half-life. By using such derivatives the monosaccharide radical thereof is acylated, especially acetylated, at the OH-groups the dosage can be further reduced to about half of the dosage. The novel recombinant glycoproteins of the invention can also be used as stimulating agents for cells of the immune system. Thus, a substantial enforcement of the immune system of immune deficient organisms is possible. They are characterized by a high cell specifity and low up to completely missing side effects as well as by a high stability, especially a high biological stability.

In the following the invention is explained in detail by referring to the specific glycoprotein rh erythropoietin, however, without being limited thereto. Of course, the following statements also apply to the other, aboved-mentioned novel recombinant glycoproteins of the invention as will be obvious to any skilled expert.

Human erythropoietin (EPO) is a glycoprotein having 166 amino acids, 3 sites of glycosylation at the positions 34, 38 and 83 of the amino acid and a molecular weight of from about 34 000 to 38 000. The proportion of the glycosyl side chains of the molecular weight is about 40% (see Jacobs et al, "Nature" 313, 806–809 (1985); and Dordal et al, "Endocrinology" 116, 2293–2299 (1985)). EPO is formed in the kidney and is transported to its physiological site of action, i.e. to the bone marrow, via the blood path.

EPO can be isolated either from natural sources like human urine (see for example Miyake et al, "J. Biol. Chem." 252, 5558–5564 (1977)), or can be produced by genetic engineering (see for example EP-A-0 148 605 and 0 267 678). Its physiological function consists in the stimulation of the erythropoieses, i.e. it stimulates the growth and the differentiation of erythrocytes precursors. It is used in a great extent as a therapeutic agent for anemia patients for post-operative patients and for patients being subjected to a homo-dialysis after a extirpation of a kidney. Primarily it serves for the therapy of renal-related anemia, i.e. for anemia caused by a restriction or a loss of the function of the kidneys. The loss of the function of the kidneys can have different reasons, for example low supply with blood, chronic inflammation, traumata, extirpation, hepatorenal syndrome and dialysis measures caused by these diseases.

A process for isolating EPO from human urine containing EPO is already known (see for example U.S. Pat. No. 3 865 801). Since, however, the content of EPO in a usual human urine is extremely low and is in the order of about 0.01 to 0.02 wt. % of the total proteins in the urine, it is difficult to produce EPO in an effective manner by this way. From EP 0 116 446 a process is already known according to which erythropoietin can be obtained in high purity and wherein a polypeptide can be used as an antibody. However, this document does not contain any indication of the obtainable yields and and moreover this process is relatively difficult to be practiced.

Since several years the gene of human EPO is known which could be isolated from a fetal liver-gene bank and characterized. Since 1985 it is available for gene technologic experiments (see Jacobs et al, "Nature" 313, 806–809 (1985)). EPO can be expressed in animal cells by using genetic engineering processes.

The novel recombinant EPO of the invention can (as also the other above-mentioned novel recombinant glycoproteins of the invention) be produced by genetic engineering starting from a pure erythropoietin obtained from an erythropoietin containing material having been recovered from cell culture supernatants. As culture cells eucaryotic cells, preferably animal cells, more preferably non-transformed or transformed CHO cells or COS7 cells or Nalm cells or fibroblasts are used which are cultivated in a manner known per se in a usual culture medium, preferably in a FCS-, RPMI 1640-, HAT-, Eagle-MEM-, Dulbecco-MEM- and/or Glasgow-MEM-medium containing as glycan precursor an N—($C_3$–$C_7$)-acylated and/or N—($C_3$–$C_7$)-hydrocarbylated monosaccharide for the biosynthesis and the thus obtained rh EPO optionally is mono- or poly- or completely acylated and preferably acetylated, respectively, at the OH groups of the monosaccharide part preferably by using a suitable acid anhydride, especially acetic acid anhydride, also in a manner known per se (see "Organicum").

Subject-matter of the present invention is according to a further aspect a process for producing of the novel recombinant glycoproteins of the invention as defined above starting from a material obtained from cell culture supernatants, the material containing one or more recombinant glycoproteins, especially recombinant human glycoproteins, which process is characterized in that as culture cells eucaryotic cells, preferably animal cells, more preferably non-transformed or transformed CHO cells or COS7 cells or Nalm cells or fibroblasts are cultivated in a manner known per se in a usual culture medium containing as a glycan precursor an N—($C_3$–$C_7$)-acylated and/or N—($C_{3-7}$)-hydrocarbylated monosaccharide for the biosynthesis of amino sugars in a concentration of from 0.001 to 50 mM/I, preferably from 0.5 to 20 mM/I, at a temperature of from 18 to 40° C., preferably of 30° C., and at a pH of from 6.0 to 8.2, preferably of 7.2, and that the thus obtained N-acyl derivative and N-hydrocarbyl derivative, respectively, of the glycoprotein is separated and recovered in a manner known per se and that optionally the OH groups and OR groups, respectively, of the monosaccharide part are mono- oder poly- or completely acylated, preferably acetylated, in a manner known per se by using preferably a suitable acid anhydride, especially acetic acid anhydride.

As the culture medium preferably an FCS-, RPMI 1640-, HAT-, Eagle-MEM-, Dulbecco-MEM- and/or Glasgow-MEM- medium is (are) used.

As an glycan precursor preferably an N—($C_3$–$C_7$)-acyl- and/or N—($C_3$–$C_7$)-hydrocarbyl-, especially N-propanoyl-, N-isopropanoyl, N-pivaloyl- and N-pivanoyl (N-tert-butylcarbonyl)-, respectively, N-cyclopropanoyl-, N-butanoyl-, N-pentanoyl-, N-hexanoyl-, N-heptanoyl-, N-crotonoyl-, N-laevulinoyl-, and/or N-propyl-, N-isopropyl-, N-pivalyl- and N-tert-butyl-, respectively, N-cyclopropyl-, N-butanyl-, N-pentanyl-, N-hexanyl-, N-heptanyl-, N-crotonyl- and N-laevulinyl-D-glucosamine, -D-galactosamine or -neuraminic acid, preferably -D-mannosamine, or a mixture thereof is (are) used.

One of the important features of the process of the invention consists in that a cell culture medium is used containing as a glycan precursor an N-acylated monosaccharide for the biosynthesis of the amino sugars, for example N-propanoyl-D-glucosamine or N-propanoyl-D-galactosamine, which are suitable to replace the N-acetyl-D-glucosamine or N-acetyl-D-galactosamine or N-acetyl-neuraminic acid by N-propanoyl-D-glucosamine or N-propanoyl-D-galactosamine or N-propanoyl-neuraminic acid in the glycan chain of the EPO dissected from the cultur cells. As particular effective the direct precursors of the neuraminic acid have been proven, namely N-propanoyl-D-mannosamine or N-butanoyl-D-mannosamine or N-pentanoyl-D-mannosamine or N-hexanoyl-D-mannosamine or N-cyclopropanoyl-D-mannosamine or a mixture of these sugars. The metabolism of these amino sugar analogues is known (see Kayser et al, "J. Biol. Chem." 267, 16934–16938 (1992)) and is as follows relating to N-propanoyl-D-mannosamine:

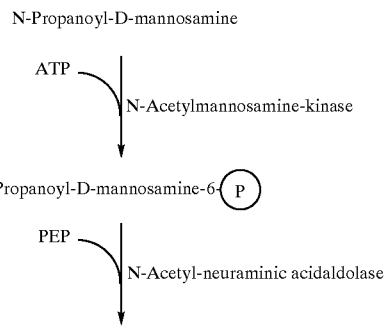

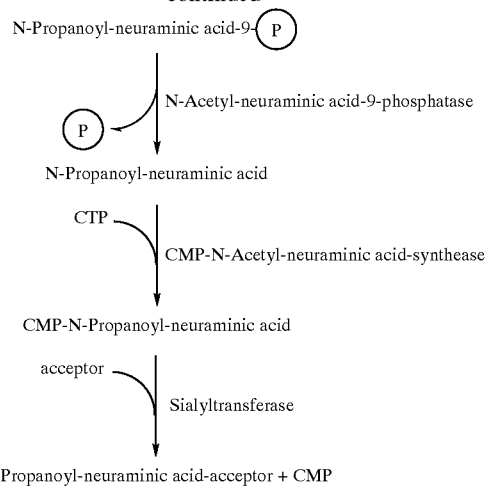

The meanings in the above reaction sequence are as follows:

| | |
|---|---|
| ATP | adenosine-triphosphate |
| PEP | phosphoenolpyruvate |
| P | phosphate |
| CTP | cytidine-triphosphate |
| CMP | cytidine-monophosphate |
| acceptor | a protein being present in a glycosylated state. |

For the glycosylation of the proteins the following monosaccharides are needed: N-acetyl-D-glucosamine, N-acetyl-D-galactosamine, D-mannose, D-galactose, L-fucose, N-acetyl-D-mannosamine and N-acetyl-neuraminic acid, which are linked with each other in a typical manner (see E. Buddecke, "Grundriβ der Biochemie", 9. edition, page 185 ff, (1994)).

The monosaccharides linked with each other to form oligosaccharides (glycans) are connected to the polypeptide either via the amino acid asparagine in the typical tripeptide sequence asparagine—any amino acid (with the exception of proline)—serine or threonine or cysteine-N-glycosidically (N-glycans) or they are linked with to each other O-glycosidically via serine (O-glycans). In these glycans N-acetyl-D-glucosamine can be replaced by N-propanoyl-D-glucosamine and/or N-acetyl-D-galactosamine can be replaced by N-propanoyl-D-galactosamine or homologous compounds like N-isopropanoyl-, N-pivaloyl- (i.e. N-tert-butylcarbonyl)-, N-cyclopropanoyl-, N-butanoyl-, N-pentanoyl-, N-hexanoyl-, N-heptanoyl-, N-crotonoyl- or N-laevulinoyl-monosaccharide or the corresponding ($C_3$–$C_7$)-hydrocarbyl derivatives. In the case of the terminal sugar N-acetyl-neuraminic acid it is replaced by the N-propanoyl- or N-butanoyl- or N-pentanoyl- or N-hexanoyl- or N-cyclopropanoyl-or N-isopropanoyl- or N-pivaloyl- or N-laevulinoyl-neuraminic acid.

The EPO synthesized in and dissected from the cells, due to the introduction of one or more of these sugar analogues which can be added as single compounds or as a mixture of compounds to the cell culture medium, exhibits a novel structure wherein the native monosaccharides are replaced by novel, chemically modified monosaccharides. The thus obtained entire compounds are novel compounds.

These metabolically modified novel erythropoietins posess novel biological properties, in particular they posess a higher biological stability. At present this can be explained by the fact that it is known that glycoproteins contain terminal N-acetyl-neuraminic acid radicals which are linked with D-galactose (see A. Rosenberg, "Biology of Sialic Acids", Plenum Press, New York and London, pages 7–67 (1995)). Their function in this linkage is to be seen therein that they protect the galactose against a recognition by cells and their galactose-specific receptors as has been shown by the experiments of G. Ashwell in the above-mentioned Schauer document. When these terminal galactoses in the glycoproteins have been recognized, the recognized glycoproteins, thus no more containing N-acetyl-neuraminic acid, are subjected to the intracellular decomposition. This N-acetyl-neuraminic acid which is essential to the biological stability is subjected to an natural turnover. It is essentially determined by the specific neuraminidases (or sialidases) splitting off the N-acetyl-neuraminic acid. This results in a growing old of these glycoproteins and they are subjected to the natural decomposition. For developing their full activity these neuraminidases need the N-acetyl group in the N-acetyl-neuraminic acid.

In the novel EPO compounds of the invention the natural N-acetyl group is replaced by homologous N—($C_3$–$C_7$)-acyl groups and/or homologous N—($C_3$–$C_7$)-hydrocarbyl groups, e.g. by the N-propanoyl group. But also the above-mentioned further N-acyl- and N-hydrocarbyl groups are effective replacement groups. The replacement of the N-acetyl-neuraminic acid by the above men-tioned homologous N-acyl compounds and N-hydrocarbyl compounds, respectively, results in a lowert affinity of the neurammini-dases to these modified N-acyl- or N-hydrocarbyl-neuraminic acids. Therefore, the modified neuraminic acid is split of in a far lowert rate, it is longer connected to the hydroprotein and can longer carrier out the desired function of protection. Therefore, the glycoprotein is biologically more stabile. This means that parenterally administrated EPO which has been modified as described above can remain for a longer perioid in the organism. Therefore, it is longer active. The dosage of EPO can be reduced since the modified EPO of the invention exhibits the same biological activity in regard to the stimulation of formation of new blood as the native EPO. Furthermore, the modified EPO of the invention is more stabile.

The above description of the biological mechanism occurring during the formation and administration of rh erythropoietin of course also applies to the other recombinant glycoproteins of the invention, i.e. to the above-mentioned coagulation factors, interferons, interleukins, growth factors, thrombolytic agents and thromboprophylactic agents.

According to a further aspect the present invention relates in particular to the following compounds:

recombinant human erythropoietin (rh erythropoietin) for the treatment of anemia, wherein the natural N-acetyl group of the glycan radicals, especially of the terminal N-acetylneuraminic acid radicals, are replaced by an N—($C_3$–$C_7$)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—($C_3$–$C_7$)-hydrocarbyl radical selected from the group consisting of N-propyl, N-isopropyl, N-pivalyl and N-tert-butyl, respectively, N-cyclopropyl, N-butanyl, N-pentanyl, N-hexanyl, N-heptanyl, N-crotonyl and N-laevulinyl; including the mono- or poly-hydroxylated and/or -ketylated analogues thereof.

The novel rh erythropoietins of the invention preferably contain a glycan radical which is selected from the group consisting of:

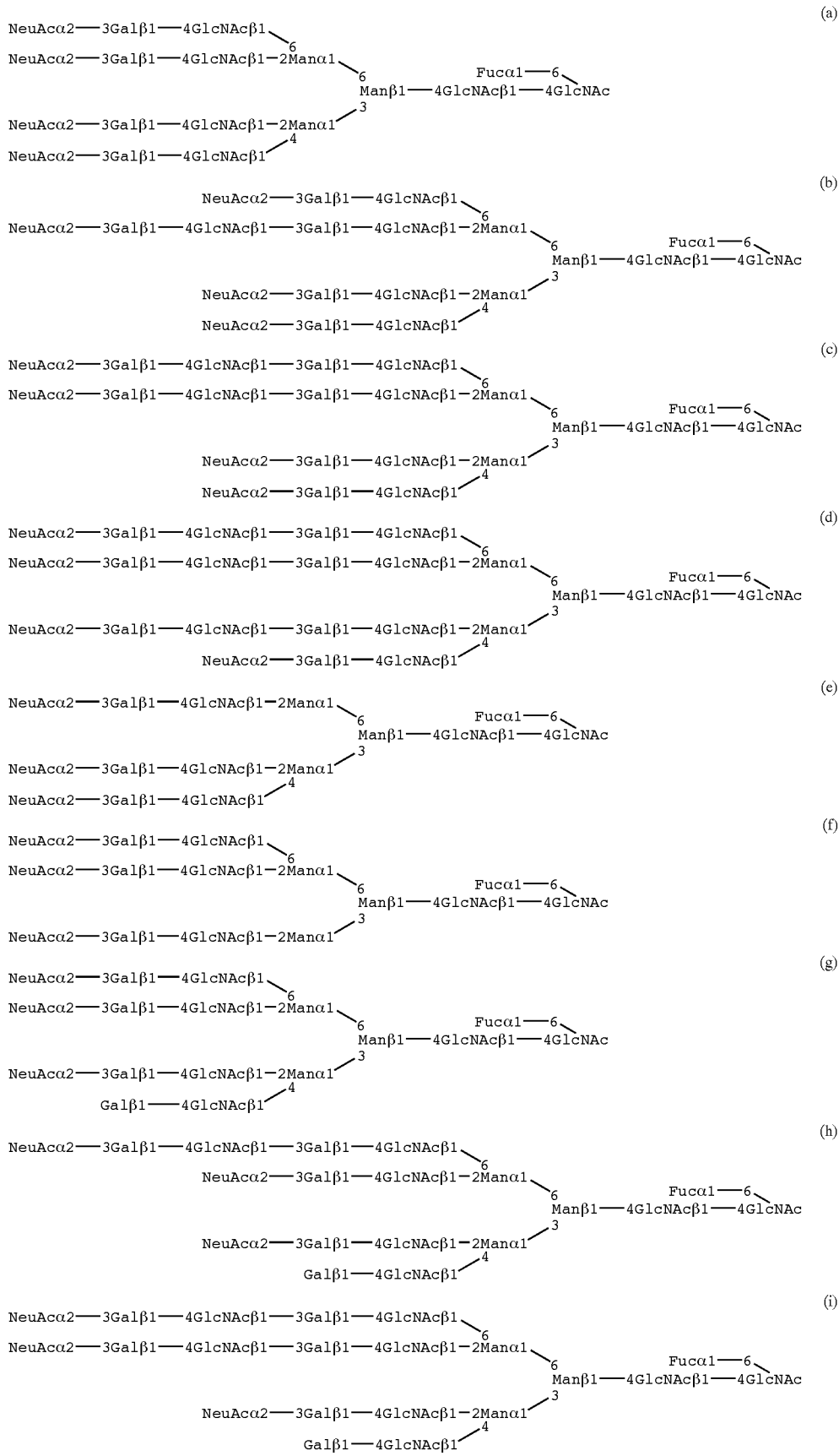

-continued

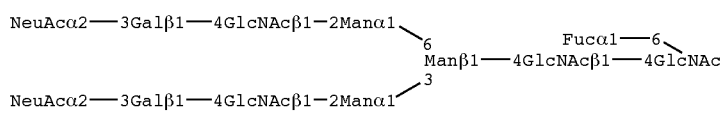
(k)

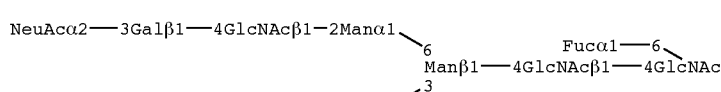
(l)

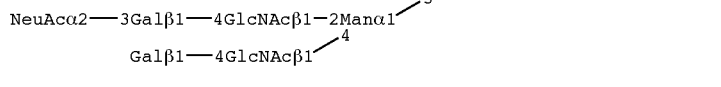
(m)

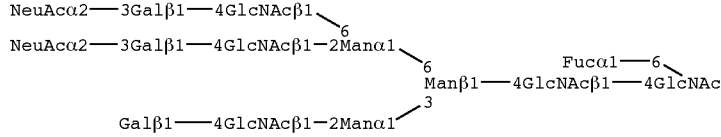
(n)

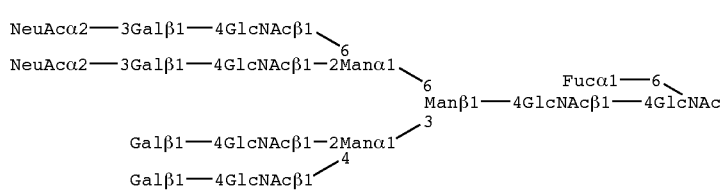
(o)

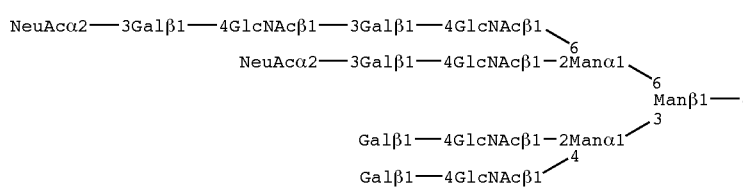

wherein Ac in the NeuAc radicals and/or one or more or all Ac in the other radicals is (are) each replaced by a $(C_3–C_7)$-acyl radical and/or a $(C_3–C_7)$-hydrocarbyl radical selected from the group consisting of propanoyl, isopropanoyl, pivaloyl and pivanoyl (tert-butylcarbonyl), respectively, cyclopropanoyl, butanoyl, pentanoyl, hexanoyl, heptanoyl, crotonoyl, laevulinoyl; propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof.

Further preferred rh glycoproteins of the invention are as follows:

rh growth factors, especially rh GCSF and/or rh GMCSF for the treatment of diseases of the blood cells formation system, especially of agranulocytosis or thrombopenia, above all for stimulating the growth of white blood cells, especially lymphocytes, granulocytes and monocytes, wherein the natural N-acetyl group of the glycan radicals, especially of the terminal N-acetylneuraminic acid radicals, is replaced by an N—$(C_3–C_7)$-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—$(C_3–C_7)$-hydrocarbyl radical selected from the group consisting of N-propyl, N-isopropyl, N-pivalyl and N-tert-butyl, respectively, N-cyclopropyl, N-butanyl, N-pentanyl, N-hexanyl, N-heptanyl, N-crotonyl and N-laevulinyl; including the mono- or poly-hydroxylated and/or -ketylated analogues thereof;

rh thrombolytic agents especially rh tPA or rh urokinase, for the treatment of thrombi or for the prophylaxis of the formation of thrombi, wherein the natural N-acetyl group of the glycan radicals, especially of the terminal N-acetylneuraminic acid radicals, is replaced by an N—$(C_3–C_7)$-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—$(C_3–C_7)$-hydrocarbyl radical, selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof;

rh thromboprophylactic agent, especially rh antithrombin III, for the prophylaxis of the formation of thrombi, wherein the natural N-acetyl group of the glycan radicals, especially of the terminal N-acetyineuramic acid radicals, is replaced by an N-$(C_3$-C7)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl und N-laevulinoyl, and/or by an N—$(C_3–C_7)$-hydrocarbyl radical selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof;

rh coagulation factors, especially rh factor VIII and/or rh factor IX, for the treatment of disorders of the coagulation system due to an inherited or acquired deficiency of factor VIII and/or factor IX, wherein the natural N-acetyl group of the glycan radicals, especially of the terminal N-acetyineuraminic acid radicals, is replaced by an N—($C_3$–$C_7$)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—($C_3$–$C_7$)-hydrocarbyl radical selected from the group consisting of propyl, isopropyl, pivalyl and tertbutyl, respectively, cyclopropyl, butanyl, pentanyl, hexanyl, heptanyl, crotonyl and laevulinyl; including the mono- or poly-hydroxylated and/or -ketylated analogues thereof.

rh interferons, especially rh a-interferon compounds, for the treatment of malignant tumors, especially melanoma, and of autoimmune diseases, wherein the natural N-acetyl group of the glycan radicals, especially of the terminal N-acetylneuraminic acid radicals, are repaced by an N—($C_3$–$C_7$)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—($C_3$–$C_7$)-hydrocarbyl radical selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof;

rh interferons, especially rh β-interferon compounds, for the treatment of all forms of multiple sclerosis and viral diseases, above all of viral hepatitis B, viral hepatitis C, viral hepatitis D and viral encephalitis, wherein the natural N-acetyl group of the glycan radicals, especially of the terminal N-acetyineuraminic acid radicals, is replaced by an N—($C_3$–$C_7$)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—($C_3$–$C_7$)-hydrocarbyl radical selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof;

rh interferons, especially rh γ-interferon compounds, for the treatment of malignant tumors, of viral hepatitis B, viral hepatitis C, viral hepatitis D and viral encephalitis, wherein the natural N-acetyl group of the glycan radicals, especially of the terminal N-acetylneuraminic acid radicals, is replaced by an N-($C_3$–$C_7$)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—($C_3$–$C_7$)-hydrocarbyl radical selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof;

rh interleukins, especially rh IL-2, rh IL-15, rh IL-16 and rh IL-17, for the treatment of malignant metastasing tumors, especially of melanoma, wherein the natural N-acetyl group of the glycan radicals, especially of the terminal N-acetylneuraminic acid radicals, is replaced by an N—($C_3$–$C_7$)-acyl radical selected from the group consisting of N-propanoyl, N-isopropanoyl, N-pivaloyl and N-pivanoyl (N-tert-butylcarbonyl), respectively, N-cyclopropanoyl, N-butanoyl, N-pentanoyl, N-hexanoyl, N-heptanoyl, N-crotonoyl and N-laevulinoyl, and/or by an N—($C_3$–$C_7$)-hydrocarbyl radical selected from the group consisting of propyl, isopropyl, pivalyl and tert-butyl, respectively, cyclopropyl, butanyl, pentanyl, hexanyl, heptanyl, crotonyl and laevulinyl; including the mono- or poly-hydroxylated and/or -ketylated analogues thereof.

The novel compounds of the invention are in particular those wherein the natural N-acetyl group of N-acetyl-D-glucosamine has been partly or completely replaced by N-propanoyl or N-cyclopropanoyl or N-isopropanoyl or N-pivaloyl and N-pivanoyl (N-tert-butylcarbonyl), respectively, or N-butanoyl or N-pentanoyl or N-hexanoyl by a biochemical modulation (biochemical engineering) by the addition of the corresponding N-acyl-D-glucosamine or N-acyl-D-galactosamine or N-acyl-neuraminic acid derivative, especially of the N-acyl-D-mannosamine derivative, to a culture medium in a final concentration in the medium of from 0.001 to 50.0 mM, especially from 0.5 to 20 mM, particularly from 0.5 to 5 mM, where in the said culture medium D-glucose can be partly or completely replaced by D-galactose; and especially those wherein the natural D-galactose has been partly or completely replaced by 2-deoxy-D-galactose by a biochemical modulation (biochemical engineering) by the addition of 2-deoxy-D-galactose to the culture medium in a final concentration in the medium of from 0.001 to 50 mM, particularly from 0.5 to 20 mM, especially from 0.5 to 5 mM.

According to a further aspect the present invention relates to pharmaceutical compositions containing, as an active ingredient, at least one rh glucosamine as defined above, optionally in combination mit other active ingredients and usual pharmaceutical vehicles and/or excipients.

Preferably the pharmaceutical compositions of the invention contain, as an active ingredient, one or more recombinant glycoproteins, especially recombinant human glycoproteins, or a mixture of differently modified N—($C_3$–$C_7$)-acyl and/or N—($C_3$–$C_7$)-hydrocarbyl derivatives thereof.

The pharmaceutical compositions of the invention contain the active rh glycoprotein ingredient which is preferably mono- or poly-acylated, especially—acetylated at the monosaccharide part, preferably in an amount of from 0.001 to 50 wt. %, preferably of from 0.1 to 20 wt. %, especially of from 2 to 10 wt. %.

Particularly preferred pharmaceutical compositions of the invention are those which contain as an active rh glycoprotein ingredient:

recombinant human erythropoietin or derivatives thereof as defined above;

rh growth factors, in particular rh CGSF and/or rh GMCSF as defined above;

rh thrombolytic agents, in particular rh tPA or rh urokinase as defined above;

rh thromboprophylactic agents, in particular rh antithrombin III, as defined above;

rh coagulation factors, in particular rh factor VIII and/or rh factor IX, as defined above;

rh interferons, in particular rh α-, β- and γ-interferons, as defined above; or rh interleukins, in particular rh IL-2, rh IL-15, rh IL-16 and rh IL-17, as defined above.

According to a further aspect the present invention relates to the use of recombinant human erythropoietin and its derivatives, as defined above, for the treatment of anemia, especially anemia related to renal diseases, in a dosage of from 0.001 to 200 mg/kg of body weight;

the use of the rh growth factors, as defined above, for the treatment of diseases of the blood cells formation system, especially of agranulocytosis or thrombopenia, above all for the stimulation of the growth of white blood cells, in particular of lymphocytes, granulocytes and monocytes, in a dosage of from 0.001 to 1.0 mg/kg of body weight;

the use of rh thrombolytic agents, as defined above, for the treatment of thrombi or for the prophylaxis of the formation of thrombi in a dosage of from 1 to 200 mg/kg of body weight, preferably from 50 to 100 mg/kg of body weight; the use of rh thromboprophylactic agents, as defined above, for the prophylaxis of the formation of thrombi in a dosage of from 1 to 200 mg/kg of body weight, preferably of from 50 to 100 mg/kg of body weight;

the use of the rh coagulation factors, es defined above, for the treatment of disorders of the coagulation system due to an inherited or acquired deficiency of factor VIII and/or factor IX, in a dosage of from 0.001 to 200, preferably from 0.1 to 50 mg/kg of body weight;

the use of rh α-interferons, as defined above, for the treatment of malignant tumors, especially of melanoma, and of autoimmune diseases in a dosage of from 0.001 to 10 μg/kg, preferably from 0.01 to 0.1 μg/kg of body weight;

the use of rh β-interferons, as defined above, for the treatment of all forms of multiple sclerosis and of viral diseases, above all of viral hepatitis B, viral hepatitis C, viral hepatitis D and viral encephalitis, in a dosage of from 0.001 to 10 μg/kg, preferably from 0.01 bis 0.1 μg/kg of body weight;

the use of rh γ-interferons, as defined above, for the treatment of malignant tumors, of viral hepatitis B, viral hepatitis C, viral hepatitis D and viral encephalitis in a dosage of from 0.001 to 0.1 μg/kg, preferably from 0.01 to 0,1 μg/kg of body weight; and the use of rh interleukins, as defined above, for the treatment of malignant metastasing tumors, especially melanoma, in a dosage of from 0.001 to 200 μg/kg of body weight.

The rh glucoproteins of the invention are preferably administered in a form the monosaccharide part thereof being mono- or poly-acylated, preferably -acetylated, at the OH groups and OR groups, respectively, where in this case the dosage of the correspondingly acylated and acetylated, respectively, derivatives can be reduced to half of the dosages mentioned in connection with the above preferred uses.

What is claimed is:

1. Recombinant glycoproteins having the formula (I)

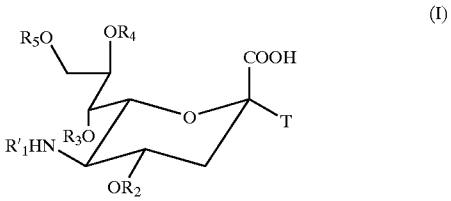

wherein:

$R'_1$ is a cyclic, optionally mono- or poly-hydroxylated and/or -ketylated ($C_3$–$C_7$)-acyl radical;

$R_2$, $R_3$, $R_4$ and $R_5$, which can be the same or different, each are hydrogen, a linear or branched alkyl radical having 1 to 20 carbon atoms; a linear or branched alkenyl radical having 3 to 20 carbon atoms; a linear or branched alkinyl radical having 3 to 20 carbon atoms; an alkenyl or alkinyl radical having 2 or more double bonds 30 and triple bonds, respectively, and having 4 to 20 carbon atoms; an aryl radical having 6 to 20 carbon atoms; a linear or branched, saturated or mono- or poly-unsaturated acyl radical (—CO—$R_1$) having in total 1 to 20 carbon atoms, including the mono- or poly-hydroxylated analogues thereof, an aroyl radical having 6 to 20 carbon atoms; a carbonylamide radical of formula —$CONH_2$ or —$CONHR_1$; a linear or branched, saturated or mono- or poly-unsaturated thioacyl radical (—CS—$R_1$) having in total 1 to 20 carbon atoms; or a thiocarbamide radical of formula (—CS—$NH_2$ or —CS—$NHR_1$;

where $R_1$ each represents hydrogen, a linear or branched, saturated or mono- or poly-unsaturated alkyl radical having 1 to 20 carbon atoms and where each of the above-mentioned radicals with the exception of H optionally can be mono- or poly-substituted by halogen, hydroxy, epoxy, amine, mercaptan, phenyl, phenol or benzyl groups and T is a mono- or di- or oligo-saccharide radical having up to 40 glycosidically linked, optionally branched sugar radicals, the saccharide radical containing furanose and/or pyranose rings and containing 5 to 230 carbon atoms and being N- or O-glycosidically bound to polypeptides.

2. The glycoproteins of claim 1, wherein in formula (I) $R_2$ $R_3$, $R_4$ and $R_5$, which can be the same or different, each represent hydrogen, a linear or branched alkyl radical having 1 to 7 carbon atoms; a linear or branched alkenyl radical having 3 to 10 carbon atoms; a linear or branched alkinyl radical having 3 to 10 carbon atoms; an alkenyl or alkinyl radical having 2 or more double bonds and triple bonds, respectively, and having 7 to 12 carbon atoms; a phenyl radical; a linear or branched, saturated or mono- or polyunsaturated acyl radical (—CO—$R_1$) having in total 1 to 7 carbon atoms, in particular an acetyl radical, including mono- or polyhydroxylated analogues thereof; an aroyl radical having 6 to 10 carbon atoms; a carbonylamide radical of formula —$CONH_2$ or —$CONHR_1$; a linear or branched, saturated or mono- or polyunsaturated thioacyl radical (—CS—$R_1$) having in total 1 to 7 carbon atoms; or a thiocarbamide radical of formula —CS—$NH_2$ or —CS—$NHR_1$;

where $R_1$ each represents hydrogen or a linear or branched, saturated or mono- or polyunsaturated alkyl radical having 1 to 20 carbon atoms and where each of the above-mentioned radicals with the exception of H optionally can be mono- or poly-substituted by fluorine, chlorine, bromine or iodine, hydroxy, epoxy, amine, mercaptan, phenyl, phenol or benzyl groups.

3. The compounds of claim 1, wherein in formula (I) T represents a saccharide radical having an N-glycan structure of formula (Ia)

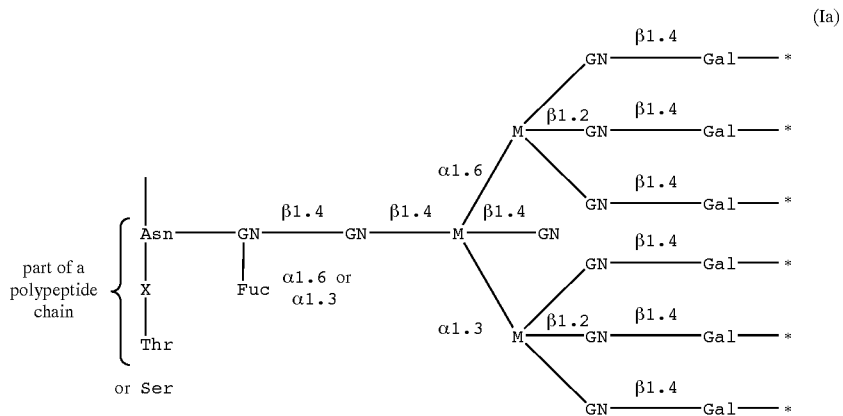

where:
Gal = galactose, GN = N-acetyl-D-glucosamine, M = D-mannose, Fuc = fucose, Asn = asparagine, X = any amine acid with the exception of proline, Thr = threonine, Ser = serine,
* = attachment side of T (1 to 6 molecule radicals), where:

Gal=galactose, GN=N-acetyl-D-glucosamine, M=D-mannose, Fuc=fucose, Asn=asparagine, X=any amino acid with the exception of proline, Thr=threonine, Ser=serine, *=attachment site of T (1 to 6 molecule radicals), in which both peripheral radicals M can be substituted by 1 to 3 trisaccharides; or T represents a saccharide radical having an O-glycan structure of formula (Ib):

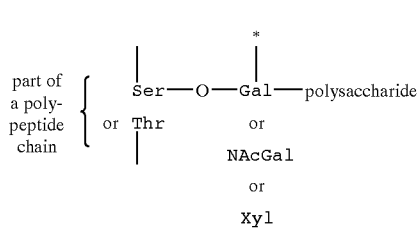

where:
Gal = galactose, Thr = threonine, Ser = serine, Xyl = xylose, NAcGal = N-acetyl-galactosamine,
* = attachment site of T, where in the above formulae (Ia) and (Ib) galactose (Gal) can be replaced by 2-deoxygalactose or 2-deoxy-2-halide (F, Cl, Br, I)-galactose.

4. The compounds of claim 1, wherein when T represents a saccharide radical having an N-glycan structure or represents a saccharide radical having an O-glycan structure, GN represents a radical of formula (II):

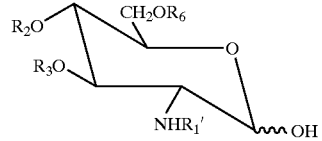

wherein $R'_1$, $R_2$ and $R_3$ have the meanings given above, $R_6$ has the same meanings as $R_2$ and $R_3$ and —$NHR'_1$ besides the equatorial position can also occupy an axial position and wherein furthermore —$OR_2$ can occupy the axial position if —$NHR'_1$ takes an equatorial position, and wherein one or more or all of the groups —$OR_2$, —$OR_3$, —$OR_6$ and/or the free OH group can be acylated by a linear or branched, saturated or mono- or polyunsaturated acyl radical (—CO—$R_1$) having in total 1 to 20.

5. The compounds of claim 4, wherein $R_1$ to $R_6$ represent H or $CH_3$ or $(C_1$–$C_7)$-acyl, especially acetyl.

6. The compound of claim 5, wherein $R_1$ to $R_6$ represent acetyl.

7. The compounds of claim 1, wherein in the $NHR'_1$-group $R'_1$ is a cyclopropanoyl.

8. The compounds of claim 1, which exhibit a modified pharmacokinetic, compared with the biological half-life time of the corresponding available natural (native) glycoproteins having a group $R'_1$=acetyl.

9. The compounds of claim 1, which are recombinant glycoproteins.

10. The compounds of claim 9 which are recombinant human glycoproteins (rh glycoprotein).

11. The compounds of claim 10 wherein the recombinant human glycoproteins are selected from rh differentiation factors, rh growth factors, rh thrombolytic agents, rh thromboprophylactic agents, rh coagulation factors, rh interferons and rh interleukins.

12. The compounds of claim 9, which are recombinant human erythropoietin (rh erythropoietin), wherein the natural N-acetyl group of the glycan radicals are replaced by an N-cyclopropanoyl radical.
13. The compounds of claim 12, which contain a glycan radical selected from the group consisting of:

-continued

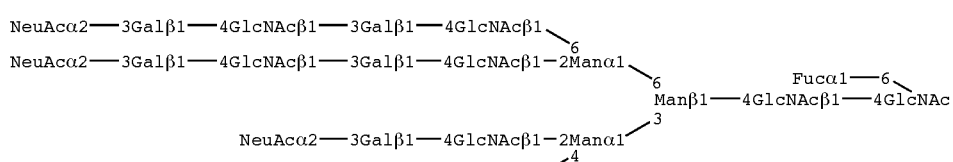

(i)

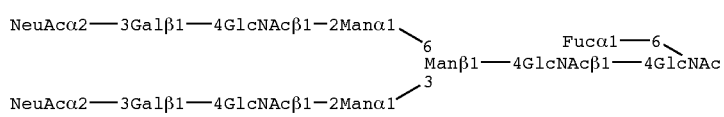

(k)

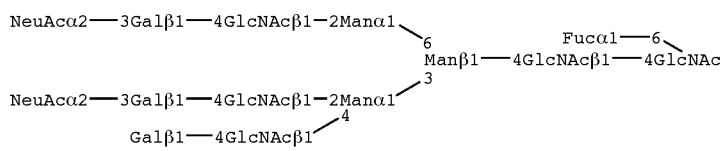

(l)

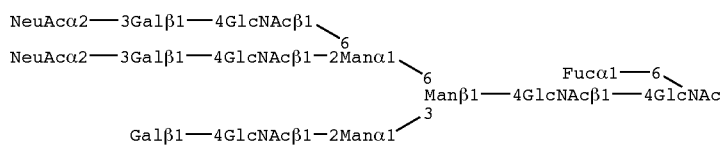

(m)

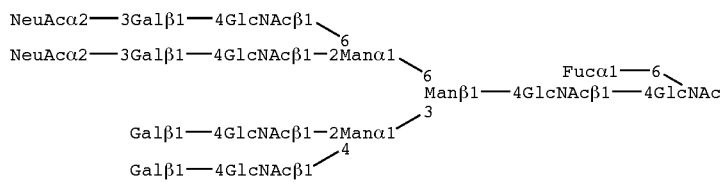

(n)

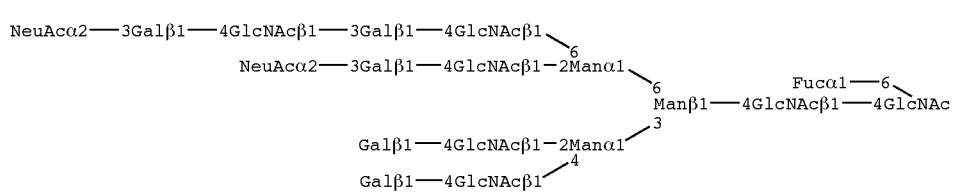

(o)

wherein Ac in the NeuAc radicals and/or one or more of all Ac in the other radicals is (are) each replaced by a cyclopropanoyl radical.

14. The compounds of claim 9, which are rh growth factors, wherein the natural N-acetyl group of the glycan radicals is replaced by an N-cyclopropanoyl radical.

15. The compounds of claim 9, which are rh thrombolytic agents, wherein the natural N-acetyl group of the glycan radicals is replaced by an N-cyclopropanoyl radical.

16. The compounds of claim 9, which are rh thromboprophylactic agents, wherein the natural N-acetyl group of the glycan radicals is replaced by an N-cyclopropanoyl radical.

17. The compounds of claim 9, which are rh coagulation factors, wherein the natural N-acetyl group of the glycan radicals is replaced by an N-cyclopropanoyl radical.

18. The compounds of claim 9, which are rh interferons, wherein the natural N-acetyl group of the glycan radicals is replaced by an N-cyclopropanoyl radical.

19. The compounds of claim 9, which are rh interleukins, wherein the natural N-acetyl group of the glycan radicals are replaced by an N-cyclopropanoyl radical.

20. The compounds of claim 9, wherein the natural N-acetyl group of N-acetyl-D-glucosamine has been partly or completely replaced by N-cyclopropanoyl by the addition of the corresponding N-cyclopropanoyl-D-glucosamine or N-cyclopropanoyl-D-galactosamine or N-acyl-neuraminic acid derivative to a culture medium in a final concentration in the medium of from 0.001 to 50.0 mM, where in the said culture medium D-glucose can be partly or completely replaced by D-galactose.

21. The compounds of claim 20, wherein said the natural D-galactose has been partly or completely replaced by 2-desoxy-D-galactose by a biochemical modulation (biochemical engineering) by the addition of 2-desoxy-D-galactose to the culture medium in a final concentration in the medium of from 0.001 to 50 mM.

22. A process for producing the recombinant glycoproteins of claim 1 starting from a material obtained from cell culture supernatants, the material containing one or more recombinant glycoproteins, the process being one wherein as culture cells eucaryotic cells are cultivated in a manner known per se in a usual culture medium containing as a glycan precursor an N-cyclopropylcarbonylated monosaccharide for the biosynthesis of aminosugars in a concentration of from 0.001 to 50 mM, at a temperature of from 18 to 40° C., and at a pH of from 6.0 to 8.2, and that the thus obtained N-cyclopropanoyl derivative of the glycoprotein is separated and recovered in a manner known per se and that optionally the OH groups and OR groups, respectively, of the monosaccharide part are mono- or poly- or completely acylated in a manner known per se by using a suitable acid anhydride.

23. The process of claim 22, wherein animal cells are utilized as eukaryotic cells.

24. The process of claim 22, wherein the cells utilized are non-transformed or transformed CHO cells or COS7 cells or Nalm cells or fibroblasts.

25. The process of claim 22, wherein as a culture medium an FCS-, RPMI1640-, HAT-, Eagle-MEM-, Dulbecco-MEM- and/or Glasgow- MEM- medium is (are) used.

26. The process of claim 22, wherein as a glycan precursor an N-cyclopropanoyl-D-glucosamine, -D-galactosamine or -neuraminic acid, or a mixture thereof is (are) used.

27. A pharmaceutical composition containing, as an active ingredient, at least one compound of claim 1, optionally in combination with other active ingredients and pharmaceutical vehicles and/or excipients.

28. The pharmaceutical composition of claim 27, which contains, as an active ingredient, one or more recombinant human glycoproteins, or a mixture of differently modified N-cyclopropanoyl derivatives thereof.

29. The pharmaceutical composition of claim 27, which contains the active ingredient in an amount of from 0.001 to 50 wt. %.

30. The pharmaceutical composition of claim 27, which contains, as an active ingredient, compounds which are recombinant human erythropoietin (rh erythropoietin), wherein the natural N-acetyl group of the glycan radicals are replaced by an N-cyclopropanoyl radical.

31. The pharmaceutical composition of claim 27, which contains, as an active ingredient, compounds which are rh growth factors, wherein the natural N-acetyl group of the glan radicals is replaced by an N-cyclopropanoyl radical.

32. The pharmaceutical composition of claim 27, which contains, as an active ingredient, compounds which are rh thrombolytic agents, wherein the natural N-acetyl group of the glycan radicals is replaced by an N-cyclopropanoyl radical.

33. The pharmaceutical composition of claim 27, which contains, as an active ingredient, compounds which are rh thromboprophylactic agents, wherein the natural N-acetyl group of the glycan radicals is replaced by an N-cyclopropanoyl radical.

34. The pharmaceutical composition of claim 27, which contains, as an active ingredient, compounds which are rh coagulation factors, wherein the natural N-acetyl group of the glycan radicals is replaced by an N-cyclopropanoyl radical.

35. The pharmaceutical composition of claim 27, which contains, as an active ingredient, compounds which are rh interferons, wherein the natural N-acetyl group of the glycan radicals is replaced by an N-cyclopropanoyl radical.

36. The pharmaceutical composition of claim 27, which contains, as an active ingredient, compounds which are rh interleukins, wherein the natural N-acetyl group of the glycan radicals are replaced by an N-cyclopropanoyl radical.

37. A method for the treatment of anemia, which comprises administering to a patient the compound of claim 12, in a dosage of from 0.001 to 200 mg/kg of body weight.

38. A method for the treatment of diseases of the blood cells formation system which comprises administering to a patient the compound of claim 14 in a dosage of from 0. 0,01 to 1.0 mg/kg of body weight.

39. A method for the treatment of thrombi or for the prophylaxis of the formation of thrombi which comprises administering to a patient the compound of claim 15 in a dosage of from 1 to 200 mg/kg of body weight.

40. A method for the prophylaxis of the formation of thrombi which comprises administering to a patient the comound of claim 16 in a dosage of from 1 to 200 mg/kg of body weight.

41. A method for the treatment of disorders of the coagulation system due to an inherited or aquired deficency of factor VIII anCd/or factor IX, which comprises administering to a patient the compund of claim 19 in a dosage of from 0.001 to 200 mg/kg of body weight.

42. A method for the treatment of malignant tumors, and of autoimmune diseases which comprises administering to a patient the compound of claim 18 in a dosage of from 0.001 to 10 µg/kg body weight.

43. A metyod for the treatment of malignant metastasing tumors, which comprises administering to a patient the compound of claim 19 in a dosage of from 0.001 to 200 µg/kg of body weight.

\* \* \* \* \*